United States Patent [19]

Elslager et al.

[11] Patent Number: 5,463,122
[45] Date of Patent: Oct. 31, 1995

[54] ARYLTHIO COMPOUNDS

[75] Inventors: Edward F. Elslager, Ann Arbor; Rocco D. Gogliotti, Pinckney, both of Mich.

[73] Assignee: Warner-Lambert Company, Morris Plains, N.J.

[21] Appl. No.: 286,816

[22] Filed: Aug. 5, 1994

[51] Int. Cl.[6] .......................... C07C 311/16; A61K 31/18
[52] U.S. Cl. ................... 564/82; 564/83; 564/86; 564/87; 564/91
[58] Field of Search ...................... 564/82, 83, 86, 564/87, 91; 514/616, 617, 618, 601

[56] References Cited

U.S. PATENT DOCUMENTS

| | | | |
|---|---|---|---|
| 3,736,280 | 5/1973 | Grivas | 260/22 A |
| 3,786,150 | 1/1974 | Lee et al. | 424/270 |
| 4,295,887 | 10/1981 | Buckley et al. | 106/18.33 |
| 4,479,950 | 10/1984 | Menard et al. | 424/248.5 |
| 4,705,805 | 11/1987 | Yamada et al. | 514/548 |
| 4,727,188 | 2/1988 | Jaedicke | 564/154 |
| 4,975,367 | 12/1990 | Albarella et al. | 435/11 |

FOREIGN PATENT DOCUMENTS

| | | |
|---|---|---|
| 0062827 | 10/1982 | European Pat. Off. . |
| 9206683 | 4/1992 | WIPO . |
| 9306832 | 4/1993 | WIPO . |

OTHER PUBLICATIONS

Abstract of "Synthesis and antibacterial activity of 2,2'-dithiobis(benzamide) derivatives against Mycobacterium species", Okachi et al, J. Med. Chem., 28(12), 1772-9, 1985.

PC93-100626, Levine et al., pp. 1-23, 1993, "Method of Inhibiting HIV Protease".

Articles, vol. 81, No. 8, Apr. 19, 1989, Weislow et al., pp. 577-586.

Primary Examiner—José G. Dees
Assistant Examiner—Dwayne C. Jones
Attorney, Agent, or Firm—Charles W. Ashbrook

[57] ABSTRACT

Antibacterial and antiviral phenylthiols and dithiobisbenzamides have the formula

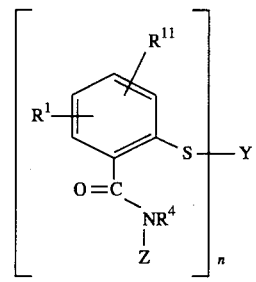

where n is 1 or 2, Y is hydrogen when n is 1, and a single bond when n is 2; and $R^1$ and $R^{11}$ are substituent groups, $R^4$ is hydrogen or alkyl, and Z is hydrogen, alkyl, cycloalkyl or sulfamoylphenyl.

9 Claims, No Drawings

ARYLTHIO COMPOUNDS

TECHNICAL FIELD OF THE INVENTION

This invention concerns compounds characterized as arylthio derivatives, and more particularly, as phenylthiols and aryl disulfides. The compounds are useful as antibacterial and antiviral agents. The compounds are especially useful in inhibiting the growth or replication of retroviruses such as human immunodeficiency virus 1 and 2 (HIV 1 and HIV 2), Simian immunodeficiency virus (SIV), Rous sarcoma virus, and human T-lymphotropic viruses 1 and 2 (HTLV 1 and HTLV 2). The compounds are useful in treating bacterial infections and viral infections.

BACKGROUND OF THE INVENTION

Bacterial infections have long been treated with effective agents such as quinolones, penicillins, and cephalosporins. However, a growing number of bacteria are becoming resistant to conventional agents, and accordingly, new drugs are needed to treat resistant strains.

Unlike bacterial infections, viral diseases have not had a wide range of agents available for treatments. While many viral infections have afflicted mankind for many years, certain diseases have only recently attracted attention due to severity and limited treatments available. Of particular importance is the viral infection known as acquired immune deficiency syndrome (AIDS).

AIDS is a very serious disease worldwide. AIDS infections have increased dramatically within the past several years. Estimates of reported cases in the very near future also continue to rise dramatically. Consequently, there is a great effort to develop drugs and vaccines to combat AIDS.

The AIDS virus was first identified in 1983. It has been known by several names and acronyms. It is the third known T-lymphocyte virus (HTLV-III), and it has the capacity to replicate within cells of the immune system, causing profound cell destruction. The AIDS virus is a retrovirus, a virus that uses reverse transcriptase during replication. This particular retrovirus is also known as lymphadenopathy-associated virus (LAV), AIDS-related virus (ARV) and, most recently, as human immunodeficiency virus (HIV). Two distinct types of HIV have been described to date, namely HIV-1 and HIV-2. The acronym HIV will be used herein to refer to HIV viruses generically.

HIV is known to exert a profound cytopathic effect on the CD4+ helper/inducer T-cells, thereby severely compromising the immune system. HIV infection also results in neurological deterioration and, ultimately in the death of the infected individual.

The field of viral chemotherapeutics has developed in response to the need for agents effective against retroviruses, in particular HIV. There are many ways in which an agent can exhibit antiretroviral activity. For example, HIV requires at least five viral proteins for replication: reverse transcriptase (RT), protease (PR), transactivator protein (TAT), integrase (IN), and regulator of virion-protein expression (REV). In addition, there are several structural proteins that play an important role in the replication and cell to cell transfer of HIV. These include the CD4 binding protein GP120, the nucleocapsid protein NCp7, and the fusion protein GP41. Accordingly, viral replication could theoretically be inhibited through binding or inhibiting any one or all of the proteins involved in the viral replication cycle.

A large number of antiretroviral agents, such as AZT, ddC, TIBO, and the like are known to inhibit RT. There also exist antiviral agents that inhibit transactivation by inhibiting the function of the protein TAT.

A useful approach being investigated recently for potential use in the treatment of AIDS is the development of synthetic peptides as inhibitors of the retroviral protease. It is known that retroviruses, including HIV, express their genetic content by directing the synthesis of a polyprotein by the host. The polyprotein is a precursor molecule, which is processed through proteolysis to generate essential viral enzymes and structural proteins. The virally encoded protease is contained within the polyprotein and is responsible for cleaving the polylprotein to yield mature viral proteins. Since the protease is known to be required for viral replication, it has been a therapeutic target for the development of AIDS drugs. These efforts have generated over 50 potent inhibitors of the protease. Several of these inhibitors are scheduled for clinical trials.

Other major efforts are underway to inhibit viral entry into target cells by identifying chemical entities that block the viral receptor. The viral fusion protein has recently been targeted for this approach. In addition, the nucleocapsid protein NCp7 has been recognized as an essential viral protein and its inhibition has been reported.

An object of this invention is to provide a new series of organic molecules which have been found to exhibit excellent antiviral activity in tests recognized to be predictive of agents useful to combat AIDS. A further object of the invention is to provide compounds having antibacterial activity. The invention additionally provides pharmaceutical compositions which are useful in treating viral and bacterial infections, and also provides a therapeutic method for treating such infections.

SUMMARY OF THE INVENTION

This invention provides arylthio compounds having antibacterial and antiviral activity. More particularly, the invention provides compounds of the Formula I

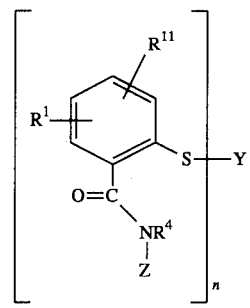

wherein:

n is 1 or 2;

Y is hydrogen when n is 1, and is a single bond when n is 2;

$R^1$ and $R^{11}$ independently are hydrogen, halo, $C_1$–$C_6$ alkyl, hydroxy, $C_1$–$C_6$ alkoxy, carboxy, $C_1$–$C_6$ alkoxycarbonyl, nitro, or $NR^2R^3$, where $R^2$ is hydrogen or $C_1$–$C_6$ alkyl and $R^3$ is hydrogen, $C_1$–$C_6$ alkyl, or $C_1$–$C_6$ alkanoyl;

$R^4$ is hydrogen or $C_1$–$C_6$ alkyl;

Z is hydrogen, $C_1$–$C_6$ alkyl, $C_3$–$C_6$ cycloalkyl, where said alkyl and cycloalkyl groups may have 1 or 2 substituents selected from hydroxy, halo, nitro, $NR^2R^3$, carboxy, and $C_1$–$C_6$ alkoxycarbonyl; and
Z is

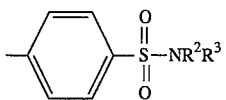

where $R^2$ and $R^3$ are as defined above;

and pharmaceutically acceptable salts and solvates thereof.

A preferred group of compounds are thiobenzamides defined by the Formula II

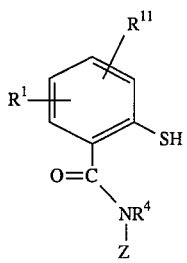

where $R^1$, $R^{11}$, $R^4$, and Z are as defined above.

Another preferred group of compounds are dithiobisbenzamides having the Formula III

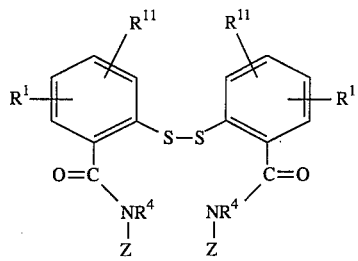

where $R^1$, $R^{11}$, $R^4$, and Z are as defined above.

The most preferred compounds are those of the above formulas wherein Z is

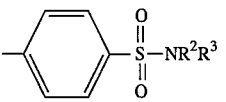

and $R^2$ is hydrogen $R^4$ in the above formulas is preferably hydrogen.

The invention also provides a pharmaceutical composition comprising a compound of Formula I together with a pharmaceutically acceptable diluent, excipient, or carrier therefor. Also provided is a method of treating bacterial infections comprising administering an antibacterially effective amount of a compound of Formula I to a subject in need of treatment. Another embodiment of the invention is a method of treating viral infections, including AIDS, comprising administering an antivirally effective amount of a compound of Formula I to a subject in need of treatment.

DETAILED DESCRIPTION

In the above formulas, $R^1$ and $R^{11}$ includes "halo", which refers to fluoro, bromo, chloro, and iodo. Preferred halo substituents are chloro and fluoro. $R^1$, $R^{11}$, and $R^4$ can be $C_1$–$C_6$ alkyl, which includes straight and branched aliphatic chains having from 1 to 6 carbon atoms. Typical alkyl groups include methyl, ethyl, isopropyl, isobutyl, tert-butyl, and n-hexyl. "$C_1$–$C_6$ alkoxy" refers to the above mentioned $C_1$–$C_6$ alkyl groups linked through an oxygen atom. Typical $C_1$–$C_6$ alkoxy groups include methoxy, ethoxy, isopropoxy, isopentyloxy, and the like. $R^1$ and $R^{11}$ also include the group $NR^2R^3$ where $R^2$ and $R^3$ can be hydrogen and alkyl, and $R^3$ can be "$C_1$–$C_6$ alkanoyl", which term includes formyl, acetyl, butyryl, and pentanoyl.

In the above formula, Z can include hydrogen, $C_1$–$C_6$ alkyl, and $C_3$–$C_6$ cycloalkyl. Typical cycloalkyl groups include cyclopropyl, cyclobutyl, and cyclohexyl. The alkyl and cycloalkyl groups defined by Z can be substituted with one or two groups selected from hydroxy, halo, nitro, amino, substituted amino ($NR^2R^3$) carboxy, and $C_1$–$C_6$ alkoxycarbonyl. Examples of such substituted alkyl and cycloalkyl groups include hydroxymethyl, chloromethyl, 3-nitrocyclopentyl, 3-carboxyhexyl, 3-methoxycarbonylcyclohexyl, 2,3-dihydroxypentyl, 3-aminopentyl, 3-acetamidopentyl, 2-hexyloxycarbonylethyl, 2-carboxycyclopropyl, 2-ethoxycarbonylcyclobutyl, and the like.

As noted above, a preferred embodiment of the invention includes thiobenzamides of Formula II

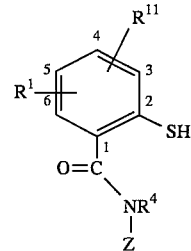

Typical compounds defined within this embodiment are those listed below.

| $R^1$ | $R^{11}$ | $R^4$ | Z |
|---|---|---|---|
| 5-OH | H | H | H |
| 4-$NO_2$ | 3-$CH_3$ | H | $CH_3$ |
| 3-$NH_2$ | 6-isopropyl | H | cyclopropyl |
| 6-fluoro | 3-chloro | —$CH_3$ | 2-methylcyclohexyl |
| 5-isobutoxy | H | —Et | 3-carboxypentyl |
| 4-methylamino | 3-ethyl | H | 3-aminopropyl |
| 5-acetamido | H | -iPr | 4-aminosulfonylphenyl |
| 4-carboxy | H | H | 4-dimethylamino-sulfonylphenyl |

Another preferred embodiment of the invention are dithiobisbenzamides of Formula III

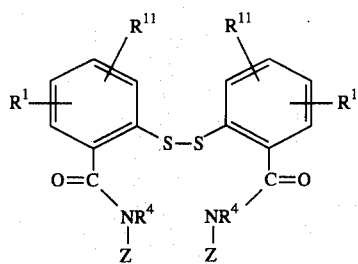   III   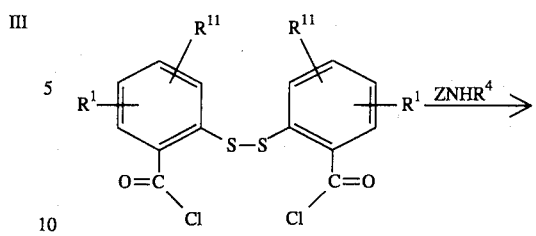

Typical examples include the following:

| R¹ | R¹¹ | R₄ | Z |
|---|---|---|---|
| 3-bromo | H | H | H |
| 4-nitro | 6-chloro | H | H |
| 5-amino | 3-methyl | —CH₃ | 3-methylpentyl |
| 5-formamido | 3-nitro | H | 3-carboxypentyl |
| 5-acetamido | H | H | H |
| 6-ethoxy | 4-fluoro | H | cyclobutyl |
| 3-isobutyl | H | —Et | methoxycarbonyl methyl |

Especially preferred compounds of the invention are those of Formula II and Formula III where Z is

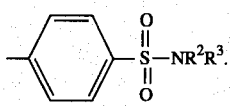

Examples of such compounds include the following:

| R¹ | R¹¹ | R² | R³ |
|---|---|---|---|
| H | H | H | acetyl |
| 3-isobutyl | H | H | methyl |
| 4-iodo | H | H | n-hexyl |
| 4-nitro | H | methyl | ethyl |
| 4-amino | 6-chloro | methyl | n-hexyl |
| 5-butyrylamino | 3-methyl | H | acetyl |
| 6-ethyl | H | H | formyl |
| 3-isopropoxy | 6-amino | methyl | propionyl |

The arylthio compounds of the invention can be prepared utilizing any of a number of synthetic processes familiar to those in the art of organic chemistry. Typically, a thiol substituted benzoic acid can be converted to a dithiobisbenzoic acid by reaction with an oxidant such as hydrogen peroxide or iodine. The dithiobisbenzoic acids are readily converted to the corresponding acid chlorides by reaction with a chlorinating agent such as thionyl chloride or oxalyl chloride. The acid chlorides are readily converted to the dithiobisbenzamides of the invention by reaction with an amine, for instance as illustrated by the following scheme:

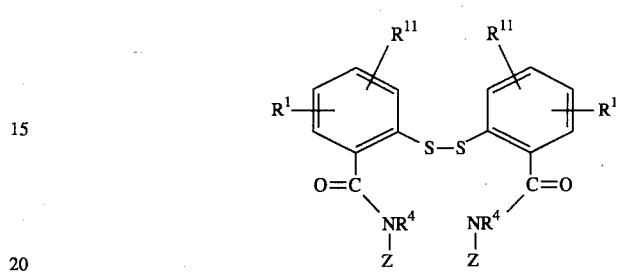

where $R^1$, $R^{11}$, $R^4$, and Z are defined above.

The amide formation reaction generally is accomplished by reacting two molar equivalents of the amine $ZNHR^4$ with one molar equivalent of the dithiobisbenzoyl chloride. The reactants normally are mixed in a mutual solvent such as dichloromethane, acetone, toluene or the like, and the reaction generally is substantially complete within 2 to 6 hours when carried out at a temperature of about 0° to 100° C. A mild base such as triethylamine or pyridine can be added to act as acid scavenger if desired. The product is readily isolated by removing the solvent, and generally, the product can be purified, if needed, by crystallization or the like.

The dithiobisbenzamides so prepared are readily converted to the thiobenzamides of the invention by reaction with a reducing agent such as 1,4-dithiothreitol, according to the following scheme:

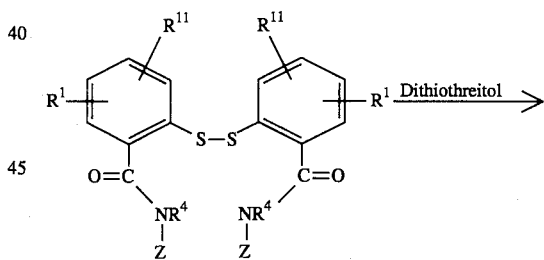

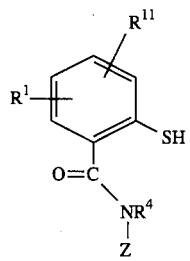

where $R^1$, $R^{11}$, and $R^4$ and Z are as defined above. The hydrolysis reaction typically is carried out in a mutual solvent such as ethanol or acetone, and normally is complete within 0.5 to 2 hours when conducted at a temperature of about 5° to about 50° C. The product thiol is readily isolated by removing the solvent and crystallizing the product.

An alternative method for preparing the dithiobisbenzamides of the invention comprises reacting a 2-halo benzamide with elemental sulfur and sodium monosulfide according to the scheme

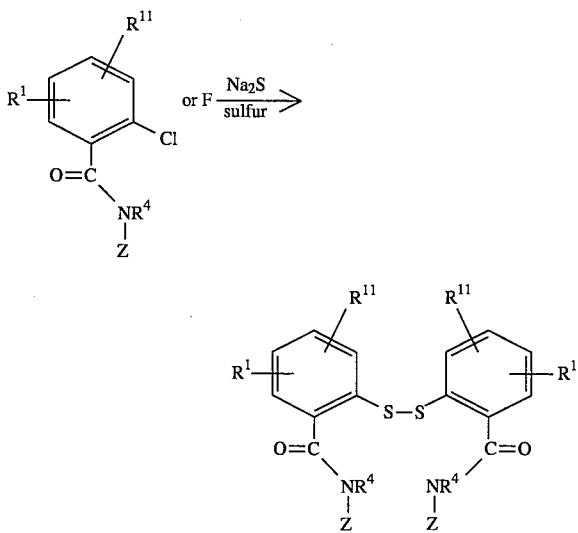

The reaction typically is carried out in a mutual solvent such as methanol or ethanol, and generally is substantially complete within 1 to 2 hours when carried out at a temperature of about 25° to about 100° C. The dithiobisbenzamide is readily isolated by removing the reaction solvent and crystallizing the product from a solvent such as isopropanol or the like.

In the above reactions, if the $R^1$ and $R^{11}$ substituents themselves are reactive, for example if $R^1$ is OH or $NH_2$, the substituents can themselves be protected to prevent unwanted side reactions according to techniques known in the art. A variety of protecting groups known in the art may be employed. For example, typical hydroxy protecting groups include substituent groups which can be added to a hydroxy, and then readily removed when desired. Such groups include acyl groups such as formyl and acetyl, as well as benzyl, trimethylsilyl, and the like. Amino groups also may need protection, and typical amino protecting groups include acyl groups such as acetyl and tert-butoxycarbonyl (BOC), and arylalkyl groups such as p-nitrobenzyl and the like. Examples of many of these typical protecting groups may be found in "Protective Groups in Organic Synthesis" by T. W. Greene, John Wiley & Sons, 1981.

Some of the reactions described above may result in mixtures of isomers. The mixtures can be separated, if desired, into the pure isomers by methods known to those skilled in the art, e.g., by fractional distillation, crystallization, and/or chromatography.

Certain of the compounds of this invention can form salts and solvates. For example, compounds wherein $R^1$ or $R^{11}$ is an amino group can react with inorganic and organic acids to form acid addition salts. Typical acids commonly employed include hydrochloric, sulfuric, acetic, malonic, paratolenesulfonic, and the like. Compounds which have an acidic group, for instance when Z contains a free carboxy group, can react with organic and inorganic bases to form salts. Typical bases include sodium hydroxide, triethylamine, pyridine, potassium carbonate, and the like.

Solvates are generally formed when crystallizing the invention compounds from solvents such as water, ethanol, isopropanol, and the like.

The synthesis of the thiobenzamides and dithiobisbenzamides of this invention is further illustrated by the following detailed examples. The examples are not to be construed as limiting the invention in any respect. The starting materials utilized in the examples are readily available from commercial sources, or can be prepared by methodologies reported in the scientific literature, for example, Bell P., *J. Am. Chem. Soc.*, 2905 (1942), describes a series of benzamides which can be utilized.

PREPARATION A 2,2'-Dithiobisbenzoyl chloride

A mixture of 2,2'-dithiobisbenzoic acid (25 g, 81.6 mmol) in 350 mL of thionyl chloride was heated at reflux for 18 hours. The resulting solution was cooled to about 30° C. and excess thionyl chloride was removed in vacuo. The crude solid was slurried in hexane and the title compound was recovered by filtration to yield 21.2 g. This compound was used without further purification, mp 150°–151° C.; NMR (CDCl$_3$): δ8.4 (m, 2H), 7.7 (d, 2H), 7.5 (m, 2H), 7.3–7.4 (m, 2H).

PREPARATION B

2-Chloro-5-nitrobenzamide

A mixture of 2-chloro-5-nitrobenzoic acid (15.0 g, 74.0 mmol) in 200 mL of dichloromethane was reacted at 24° C. with oxalyl chloride (16.2 mL, 186.0 mmol) and a catalytic amount of dimethylformamide. After 3 hours, the solvent was removed in vacuo, and the residue was redissolved in 200 mL of fresh dichloromethane. The solution was cooled to 0° C., and ammonia was bubbled into the solution for 5 minutes, whereupon the product precipitated from solution. The product was collected by filtration to yield 6.8 g of 2-chloro-5-nitrobenzamide, mp 174°–175° C.; NMR (DMSO-d$_6$): δ8.2 (m, 2H), 8.2 (s, 1H), 7.8–7.9 (m, 2H).

EXAMPLE 1

2,2'-Dithiobis-4'-[sulfamoylbenzanilide] (general method)

A solution of 2,2'-dithiobisbenzoyl chloride (5.0 g, 14.0 mmol) in 50 mL of dichloromethane was added dropwise to a solution of 4-(aminosulfonyl)aniline (6.2 g, 36.0 mmol) in 125 mL of pyridine cooled to 0° C. The mixture was stirred for 18 hours at 0° C., and the resulting solid was removed by filtration, washed with 1N HCl, water, and dried in vacuo to yield 7.6 g of crude product. This crude material (6.5 g) was suspended in 50 mL dimethylformamide/60 mL ethanol, filtered, and precipitated from the filtered solution by the addition of 10 mL 4% aqueous NaHCO$_3$. The product was collected by filtration, washed with ethanol and water to yield 4.3 g of the title compound, mp 311°–312° C.; NMR (DMSO-d$_6$): δ10.9 (s, 2H), 7.7–8.0 (m, 12H), 7.5 (m, 2H), 7.4 (m, 2H), 7.3 (s, 4H).

EXAMPLE 2

2,2'-Dithiobis-N-[4-[(methylamino)sulfonyl]phenyl]benzamide

This compound was prepared according to the general method of Example 1 using 2,2'-dithiobisbenzoyl chloride (2.2 g, 6.0 mmol) in 15 mL of dichloromethane and 4-[(methylamino)sulfonyl]aniline (3.0 g, 16.0 mmol) in 20 mL of pyridine. The crude product was recrystallized from dimethylformamide, ethanol, and 4% aqueous NaHCO$_3$ to afford 1.9 g of the title compound, mp 245°–247° C.; NMR (DMSO-$d_6$): δ10.9 (s, 2H), 7.9 (m, 4H), 7.7–7.8 (m, 8H), 7.5 (m, 2H), 7.3–7.4 (m, 6H), 2.4 (m, 6H).

EXAMPLE 3

2,2'-Dithiobis-N-[4-[[(1-methylethyl)amino]sulfonyl]phenyl]benzamide

This compound was prepared according to the general method of Example 1 using 2,2'-dithiobisbenzoyl chloride (1.3 g, 3.0 mmol) in 30 mL of dichloromethane and 4-[(1-methylethylamino)sulfonyl]aniline in 30 mL pyridine. The crude product was recrystallized from dimethylformamide, ethanol, and water to yield 0.7 g of the title compound, mp 146°–148° C.; NMR (DMSO-$d_6$): δ10.9 (s, 2H), 7.9 (d, 4H), 7.7–7.8 (m, 8H), 7.5 (m, 4H), 7.4 (m, 2H), 3.2 (m, 2H), 0.9 (d, 12H).

EXAMPLE 4

2,2'-Dithiobis-N-[4-[(acetylamino)sulfonyl]phenyl]benzamide

The compound was prepared according to the general method of Example 1 using 2,2'-dithiobisbenzoyl chloride (3.0 g, 8.0 mmol) in 30 mL of dichloromethane and 4-[(acetylamino)sulfonyl]aniline (5.6 g, 26.0 mmol) in 100 mL of pyridine. The crude product was purified by chromatography on a silica gel column using chloroform/methanol (1:1 v/v) as the mobile phase. The pure fractions were pooled, concentrated in vacuo to provide a solid, which was then recrystallized from ethanol/water (1:1 v/v) to yield 0.5 g of 2,2'-dithiobis-N-[4-[(acetylamino)sulfonyl]phenyl)-benzamide, mp 180°–182° C.; NMR (DMSO-$d_6$): δ12.0 (b, 2H), 11.0 (s, 2H), 7.8–8.0 (m, 16H), 7.5 (m, 2H), 7.4 (m, 2H), 1.9 (s, 6H).

EXAMPLE 5

2-[[2-[(1-Carboxy-2-methylbutylcarbamoyl)phenyldisulfanyl]-benzoyl]-amino]-3-methylpentanoic acid Racemic iso-leucine (26.2 g, 0.2 mol) was slurried in 100 mL of absolute ethanol and treated with a solution of sodium (4.6 g, 0.2 mol) in 100 mL of ethanol, then cooled to −50° C. 2,2'-Dithiobisbenzoyl chloride (17.2 g, 0.5 mol) was added portionwise and the solution was stirred for 18 hours. The solvent was removed in vacuo and the solid was dissolved in water and filtered to remove any insoluble material. The compound was precipitated from the filtrate with the addition of 1N HCl to a final pH=3 and collected by filtration. The product was again dissolved in water using NaHCO$_3$, treated with charcoal, filtered, and precipitated with the addition of 1N HCl to pH=3. This procedure was repeated again to yield 8.9 g of the title compound. The compound was recrystallized from 60% aqueous ethanol to afford 1.3 g of the title compound, mp 216°–218° C.; NMR (DMSO-$d_6$): δ12.7 (s, 2H), 8.6–8.8 (m, 2H), 7.6 (m, 4H), 7.4 (m, 2H), 7.3 (m, 2H), 4.3–4.6 (m, 2H), 2.0 (m, 2H), 1.5 (m, 2H), 1.3 (m, 1H), 0.9 (m, 12H).

EXAMPLE 6

2-Thio-N-(4-sulfamoylphenyl)benzamide 2,2'-Dithiobis (4'-sulfamoyl)benzanilide (0.1 g, 0.2 mmol) was dissolved in 4 mL of dimethylformamide and 1.6 mL of 2.7% NaH$_2$PO$_4$. Dithiothreitol (0.1 g, 0.7 mmol) was added, and the mixture was allowed to stir for 0.5 hours. Formic acid (10 mL 10% aqueous) was added to precipitate the product, which was collected by filtration, washed with water and diethyl ether to yield 72 mg of 2-thio-N-(4-sulfamoylphenyl)benzamide, mp 230°–231° C.; NMR (DMSO-$d_6$): δ10.7 (s, 1H), 7.9–7.7 (m, 4H), 7.6 (d, 1H), 7.5 (d, 1H), 7.4 (m, 1H), 7.3–7.2 (m, 3H).

EXAMPLE 7

2,2'-Dithiobis-5-nitrobenzamide

2-Chloro-5-nitrobenzamide (6.8 g, 33.0 mmol) was heated to reflux in 90 mL of ethanol and treated portionwise with Na$_2$S.9H$_2$O (2.6 g, 20.5 mmol) and sulfur (0.7 g, 20.5 mmol). The mixture was heated at reflux for 1 hour, then cooled to room temperature, whereupon a solid formed. The solid was removed by filtration to yield 2.6 g of the title compound, mp 266°–269° C.; NMR (DMSO-$d_6$): δ8.7 (s, 2H), 8.7 (s, 2H), 8.3 (m, 2H), 8.0 (s, 2H), 7.8 (m, 2H).

EXAMPLE 8

2,2'-Dithiobis-5-aminobenzamide 2,2'-Dithiobis-5-nitrobenzamide (2.6 g, 7.0 mmol) from Example 7 was added portionwise to a refluxing slurry of reduced iron (8.7 g) in 65 mL of water containing 0.1 mL of acetic acid. The resulting slurry was heated at reflux for 2 hours, then cooled to room temperature. The slurry was made strongly basic (pH=10) by the addition of 14 mL of 1N NaOH and filtered. Acetic acid was added to the solution to obtain a pH=7. While bubbling oxygen into the solution, a pH=6–7 was maintained with the addition of acetic acid. A solid gradually formed and was filtered to yield 1.1 g of 2,2'-dithiobis-5-aminobenzamide, mp 188°–190° C.; NMR (DMSO-$d_6$): 7.7 (s, 2H), 7.2–7.3 (m, 4H), 6.5–6.6 (m, 4H), 5.3 (s, 4H).

EXAMPLE 9

2,2'-Dithiobis(5-acetylamino)benzamide 2,2'-Dithiobis-5-aminobenzamide (1.1 g, 3.4 mmol) from Example 8 was dissolved in 6 mL of glacial acetic acid on a steam bath and treated with acetic anhydride (0.7 mL, 7.2 mmol). Upon cooling, the product precipitated from solution. An additional 4 mL of glacial acetic acid and 0.1 mL of acetic anhydride was added, and the mixture was heated at reflux for 10 minutes. The mixture was cooled to room temperature. The crude product was recovered by filtration and recrystallized from a mixture of dimethylformamide:dimethyl sulfoxide:water (30:30:40 v/v/v) to yield 0.8 g of 2,2'-dithiobis-(5-acetylamino)-benzamide), mp 301°–303° C.; NMR (DMSO-$d_6$): δ10.1 (s, 2H), 8.0 (s, 2H), 7.8 (s, 2H), 7.5 (s, 6H), 2.0 (s, 6H).

EXAMPLE 10

5-Acetylamino-2-thiobenzamide 2,2'-Dithiobis-5-(acetamidobenzamide) from Example 9 (80 mg, 0.2 mmol) was partially dissolved in 3 mL of dimethylformamide and 1.5 mL 2.7% NaH$_2$PO$_4$. A homogeneous solution was realized with the addition of dithiothreitol (0.1 g, 0.7 mmol) and after 20 minutes, 10 mL of 10% acetic acid was added. The solvents were removed in vacuo, the residue slurried in water, and the solid removed by filtration to yield 22 mg of the title compound, mp 148°–149° C.; NMR (DMSO-$d_6$): δ10.0 (s, 1H), 7.9 (s, 1H), 7.7 (s, 1H), 7.5 (m, 2H), 7.3 (d, 1H), 5.2 (s, 1H), 2.0 (s, 3H).

The compounds of this invention have been found to be active as antibacterial agents and as antiviral agents. The compounds are thus useful as pharmaceuticals as well as industrial disinfectants. The test systems utilized to establish the antiviral activity of the arylthio compounds of this invention are well recognized in the art and are routinely employed for such purpose. For example, the assay utilized to evaluate the compounds activity against the HIV virus is that employed by the U.S. National Cancer Institute as described by Weislow O. S., et al., *J. Natl. Cancer Inst.*, 81:577–586 (1989), incorporated herein by reference.

The procedure is designed to detect agents acting at any stage of the virus reproductive cycle. The assay basically involves the killing of T4 lymphocytes by HIV. Small amounts of HIV are added to cells, and at least two complete cycles of virus reproduction are necessary to obtain the required cell killing. Agents which interact with virions, cells, or virus gene-products to interfere with viral activities will protect cells from cytolysis. The system is automated in several features to accommodate large numbers of candidate agents, and is generally designed to detect anti-HIV activity. However, compounds which degenerate or are rapidly metabolized in the culture conditions may not show activity in this screen.

Another test system utilized to evaluate the invention compounds is called HIV H9 assay. The HIV H9 cell assay measures the inhibitor concentration required to suppress HIV-1 virus replication. In this system, viral growth occurs through multiple rounds of the life-cycle. Any suppression of the replication kinetics results in a geometric decrease in virus production. As a result, this assay is a sensitive means of measuring the ability of a compound to inhibit HIV-1 viral replication.

The H9 T-cell line is batch infected with HIV virus at an MOI of 0.01. After 2 hours absorption, the cells are washed, resuspended in RPMI-1640/10% fetal calf serum, and seeded at 5×10-3 cells/well of a 96-well plate. A duplicate plate of uninfected H9 cells is prepared for the cytotoxicity assay. Drugs are serially diluted 1/3.16 in DMSO, transferred to media at an 8× concentration, and then added to the cultures in triplicate. The final DMSO concentration of 0.002 (0.2%).

Viral production is measured by RT assay and cytotoxicity is measured by XTT assay at 7 days post-infection. The RT assay is performed as a modification of Borroto-Esoda and Boone, *J. Virol.*, 65:1952–1959 (1991) and quantitated using a Molecular Dynamics Phosphoimager with Imagequant software. The XTT assay is performed as a modification of Roehm, et al., *J. Immuno. Methods.*, 142:257–265 (1991) and quantitated using a molecular Devices Thermomax plate reader with Softmax software.

Data is electronically transferred to a Microsoft Excell spreadsheet for analysis. The RT assay values equivalent to 50% and 90% inhibition of virus production are calculated from the untreated controls. The concentrations of inhibitor required to produce these values ($IC_{50}$ and $IC_{90}$) are interpolated from data points flanking these RT activities. The XTT assay values equivalent to 50% cytotoxicity are calculated from the untreated controls. The concentrations of inhibitor required to produce this value are interpolated from data points flanking these XTT values.

Yet another test system employed to determine antiviral activity is called the CEM cell assay.

T4 lymphocytes (CEM cell line) are exposed to HIV at a virus to cell ratio approximately 0.05, and plated along with noninfected control cells in 96-well microliter plates.

Candidate agent is dissolved in dimethyl sulfoxide (unless otherwise noted), then diluted 1:200 in cell culture medium. Further dilutions (half-$log_{10}$) are prepared before adding to an equal volume of medium containing either infected or noninfected cells.

Cultures are incubated at 37° in a 5% carbon dioxide atmosphere for 6 or 7 days. The tetrazolium salt, XTT, is added to all wells, and cultures are incubated to allow formazan color development by viable cells (*J. National Cancer Institute*, 81:577–586 (1989)). Individual wells are analyzed spectrophotometrically to quantitate formazan production, and in addition are viewed microscopically for detection of viable cells confirmation of protective activity.

Drug-tested virus-infected cells are compared with drug-treated noninfected cells and with other appropriate controls (untreated infected and untreated noninfected cells, drug-contain wells without cells, etc.) on the same plate. Data are reviewed in comparison with other tests done at the same time and a determination about activity is made.

Table 1 below presents data for several invention compounds when evaluated in the H9 and the CEM cell assays. The data establish the compounds of this invention are effective against the HIV virus when evaluated in both test systems.

TABLE 1

| | Anti-HIV-1 Activity | | | |
| | H9 Cell Assay | | CEM Cell Assay | |
| Compound of Example No. | $EC_{50}^a$ (μM) | $IC_{50}^b$ (μM) | $EC_{50}^a$ (μM) | $IC_{50}^b$ (μM) |
| --- | --- | --- | --- | --- |
| 1 | 0.7 | 36 | 2.9 | >120 |
| 4 | 4.8 | 27 | | |
| 5 | 1.4 | 62 | 10.5 | 105 |
| 6 | 2.5 | 28 | 5.2 | >100 |
| 9 | 1.70 | >100 | 5.2 | >120 |
| 10 | 5.40 | >100 | | |

[a] Effective Concentration which protects cells from viral cytopathic effects.
[b] Inhibitory Concentration where drug alone inhibits cell growth.

The compounds of the invention were also evaluated against various other HIV strains and cell lines utilizing the assay methodology described above. The compounds were additionally evaluated against clinical isolates of HIV strains. Table 2 presents the results of such testing, and also presents activity for the known anti-HIV agents ddI (dideoxyinosine) and AZT. The data establish the compounds of this invention are potent antiviral agents, and have excellent activity against numerous HIV strains, including some which are resistant to known treatments such as AZT.

TABLE 2

| | | Activity vs. Other HIV Strains and Cell Lines | | | | |
| Cell | | $EC_{50}$ (μM) | | | | |
| Line | Virus | Example 1 | Example 4 | Example 9 | ddI | AZT (nM) |
| --- | --- | --- | --- | --- | --- | --- |
| CEM | HIV-$1_{RF}$ | 2.3 | 1.5 | 0.4 | — | 0.6 |
| CEM | HIV-$1_{II\,rb}$ | 2.8 (4.6) | 5.2 | 0.4 | — | 4.5 |

TABLE 2-continued

Activity vs. Other HIV Strains and Cell Lines

| Cell Line | Virus | EC$_{50}$ (μM) | | | | |
|---|---|---|---|---|---|---|
| | | Example 1 | Example 4 | Example 9 | ddI | AZT (nM) |
| MT-2 | HIV-1$_{II\,rb}$ | 2.6 | — | 9.4 | 6.0 | — |
| MT-2 | HIV-1$_{A17}$ | 0.6 | — | — | 4.6 | — |
| MT-4 | HIV-1$_{6R}$ | 1.9 | 1.9 | — | — | >1000 |
| MT-4 | HIV-1$_{A17}$ | 0.6 | 8.9 | 2.4 | — | 114 |
| CEM | HIV-1$_{N119}$ | 2.2 | 4.6 | 2.3 | — | 44.4 |
| CEM | HIV-2$_{ROD}$ | 2.6 | 3.0 | 1.0 | — | 1.41 |
| CEM | SIV | 14.6 | 3.4 | 2.1 | — | 245 |
| AA5 | HIV-1$_{II\,rb}$ | 0.9 | — | 3.5 | — | — |
| Clinical Isolates | | | | | | |
| PBL | HIV-1$_{VIHU}$ | 3.6 | — | 5.2 | — | — |
| PBL | HIV-1$_{WEIO}$ | 3.5 | 5.2 | 7.5 | — | 3.0 |
| PBL | HIV-1$_{BAKI}$ | 0.3 (0.25) | — | 1.8 | — | — |
| PBL | HIV-1$_{WOME}$ | 4.0 | — | 5.7 | — | — |

The compounds of the invention have utility against a wide range of retroviral infections, and accordingly, have broad application. Examples of possible viruses that may be suitable for treatment using the present invention include Type C and Type D retroviruses, HTLV-1, HTLV-2, FLV, SIV, MLV, BLV, BIV, equine infectious viruses, anemia viruses, arian sarcoma viruses, and the like.

The compounds are additionally useful as broad spectrum antibiotics. Table 3 below presents typical antibacterial activity for the compounds of this invention. Minimum inhibitory concentrations were determined utilizing microtitration techniques described by Heifetz, et. al., *Antimicrobial Agents and Chemotherapy*, 1974, Vol. 6, 124. The data establish that the compounds have activity against a broad spectrum of bacteria, both Gram+ and Gram−. Accordingly, the compounds can be utilized to treat and prevent bacterial diseases in animals and humans. They can also be used as industrial disinfectants, for example, to reduce bacterial growth in shower stalls and public areas.

TABLE 3

Antibacterial Activity

| Compound of Example No. | Gram (−) | | Gram (+) | |
|---|---|---|---|---|
| | E. coli MC4100 | E. coli B90 | B. subtilis RBI | Stah. aureus RBI | Strep. pyogenes c-203 |
| 4 | 128 | 32 | 128 | 256 | 64 |
| 6 | 64 | 32 | 128 | 128 | 64 |

In a further embodiment of this invention, the compounds can be formulated into compositions suitable for applying to surfaces such as wood, metal, ceramic, and the like, and for administering to animals, including humans, for treating and preventing diseases caused by bacteria and viruses. The compounds can be formulated for administration by any route, for instance orally, parenterally, topically, and rectally. For oral administration, for example, an invention compound can be mixed with an inert diluent or with an assimilable edible carrier, or it may be enclosed in a hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5% to about 80% of the weight of the unit. The amount of active compound in such therapeutically useful compositions is such that a therapeutically effective dosage will be obtained. Preferred compositions or preparations according to the present invention are prepared so that an oral dosage unit form contains between about 5 and 1000 mg of active compound, and ideally about 25 to about 750 mg.

The tablets, troches, pills, capsules, and the like may also contain common pharmaceutical excipients such as binders, sweeteners, and the like. Typical binders include gum tragacanth, acacia, corn starch, and gelatin, as well as excipients such as dicalcium phosphate. Typical disintegrating agents include corn starch, potato starch, alginic acid, and the like. A commonly used lubricant is magnesium stearate. Typical sweetening agents are sucrose, lactose, or saccharin, and flavoring agents such as peppermint, oil of wintergreen, or cherry flavoring can be utilized. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. A syrup or elixir may contain the active compound, sucrose as a sweetening agent, methyl and propylparabens as preservatives, a dye, and flavoring such as cherry or orange flavor. Of course, any material used in preparing any dosage unit form should be pharmaceutically pure and substantially nontoxic in the amounts employed.

The arylthio compounds of the invention can also be formulated for topical administration, for instance as patches, salves, creams, ointments, and the like. Agents commonly utilized to enhance transdermal passage can also be employed. The compounds can also be formulated with waxes and the like for convenient rectal administration.

The active compound may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a polyol (for example, glycerol, propylene glycol, and liquid polyethylene glycol, and the like), suitable mixtures thereof, and vegetable oils. The proper fluidity can be maintained, for example, by the use of a coating such as lecithin; by the maintenance of the required particle size in the case of dispersion and by the use of surfactants. the prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from about 5 to about 1000 mg, with from about 25 to about 750 mg being preferred. Expressed in proportions, the active compound is generally present in from about 10 to about 750 mg/mL of carrier. In the case of compositions containing supplementary active ingredients, the dosages are determined by reference to the usual dose and manner of administration of the said ingredients. The unit dosages typically will be administered from one to four times per day, or as otherwise needed to effect treatment of the disease state.

The following examples further illustrate the formulations of this invention.

EXAMPLE 11

Soft gelatin capsules were prepared using the following ingredients:

|  | Quantity (mg/capsule) |
| --- | --- |
| Compound of Example 1 | 250.0 |
| Butylated hydroxyanisole B.P. | 0.05 |
| Fractionated Coconut Oil B.P. | 70.0 |
|  | 320.05 |

The above ingredients were mixed and filled into a soft gelatin capsule, the shell components of which were gelatin and glycerine. The capsules are administered at the rate of one to four times a day.

EXAMPLE 12

Tablets are prepared using the following components:

| Compound of Example 5 | 500 mg |
| --- | --- |
| Microcrystalline Cellulose | 200 mg |
| Sodium Carboxymethyl Starch | 20 mg |
| Magnesium Stearate | 4 mg |
| Butylated Hydroxyanisole B.P. | 0.002 mg |

The ingredients were blended to uniformity and compressed into a tablet for oral administration. One to four tablets are administered daily for treatment of bacterial and viral infections.

EXAMPLE 13

| Compound of Example 4 | 100 mg |
| --- | --- |
| Propylene glycol | 20 mg |
| Dichlorotetrafluoroethane (Propellant 14) | 600 mg |
| Dichlorodifluoromethane (Propellant 12) | 500 mg |

The components are mixed at −20° C. and placed into a sealed can equipped with a metering device.

EXAMPLE 14

A solution is prepared as follows:

| Compound of Example 6 | 5 mg |
|---|---|
| Water | 1 L |
| 1N HCl | 20 mL |

The ingredients are mixed to form a solution which can be utilized to wash shower stalls in order to prevent and eliminate bacterial growth.

A further embodiment of this invention is a method of treating, preventing, and combatting bacterial and viral infections. The method comprises administering an antibacterially effective or antivirally effective amount of a compound of this invention to a subject or surface in need of treatment. For example, the compounds of Formula I can be applied to shower stalls and public places in order to prevent, control, and combat bacterial and viral growth. The compounds can be administered to animals, especially humans, to treat and prevent bacterial and viral infections. As noted above, an effective amount of the active compound generally is about 5 to about 1000 mg per dosage unit, and ideally about 25 to about 750 mg.

The active ingredients of the therapeutic compositions and the compounds of the present invention exhibit excellent antiretrovirus activity when administered in amounts ranging from about 1.0 to about 100 mg/kg of body weight per day. A preferred dosage regimen for optimum results would be from about 2.0 to about 50 mg/kg of body weight per day, and such dosage units are employed so that a total of from about 0.2 to about 3.0 g of the active compound for a subject of about 70 kg of body weight are administered in a 24-hour period. This dosage regimen may be adjusted to provide the optimum therapeutic response and is preferably administered one to four times a day in dosages of about 250 to about 750 mg per administration. For example, several divided doses may be administered daily or the dose may be proportionally reduced as indicated by the exigencies of the therapeutic situation. A decided practical advantage is that the active compound may be administered in a convenient manner such as by the oral, intravenous (where water soluble), intramuscular or subcutaneous routes.

The active compounds can be formulated as aqueous solutions and suspensions for washing surfaces such as wood, steel, ceramic, and the like in order to eliminate and control growth due to bacteria and viruses.

We claim:
1. A compound of the formula

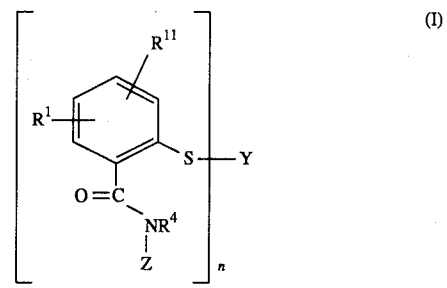

wherein:

n is 1 or 2;

Y is hydrogen when n is 1, and is a single bond when n is 2;

$R^1$ and $R^{11}$ independently are hydrogen, halo, $C_1$–$C_6$ alkyl, hydroxy, $C_1$–$C_6$ alkoxy, carboxy, $C_1$–$C_6$ alkoxycarbonyl, nitro, or $NR^2R^3$, where $R^2$ is hydrogen or $C_1$–$C_6$ alkyl and $R^3$ is hydrogen, $C_1$–$C_6$ alkyl or $C_1$–$C_6$ alkanoyl;

$R^4$ is hydrogen or $C_1$–$C_6$ alkyl;

Z is

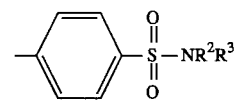

where $R^2$ and $R^3$ are as defined above;

and pharmaceutically acceptable salts and solvates thereof.

2. A compound of claim 1 wherein n is 2 and y is a single bond.

3. A compound of claim 2 wherein $R^2$ is hydrogen.

4. The compound of claim 3 which is 2,2'-dithiobis-4'-[sulfamoylbenzanilide].

5. The compound of claim 3 which is 2,2'-dithiobis-N-[4-[(methylamino)sulfonyl]phenyl]benzamide.

6. The compound of claim 3 which is 2,2'-dithiobis-N-[4 [[(1-methylethyl)amino]sulfonyl]phenyl]benzamide.

7. The compound of claim 3 which is 2,2'-dithiobis-N-[4-[(acetylamino)sulfonyl]phenyl]benzamide.

8. A pharmaceutical composition comprising a compound of claim 1 admixed with a diluent, carrier, or excipient therefor.

9. The formulation of claim 8 employing a compound wherein n is 2 and Y is a single bond.

* * * * *